(12) United States Patent
Kim

(10) Patent No.: US 7,838,273 B2
(45) Date of Patent: Nov. 23, 2010

(54) BIOMOLECULAR HYBRID MATERIAL AND PROCESS FOR PREPARING SAME AND USES FOR SAME

(75) Inventor: Jungbae Kim, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 396 days.

(21) Appl. No.: 12/053,373

(22) Filed: Mar. 21, 2008

(65) Prior Publication Data
US 2008/0318294 A1    Dec. 25, 2008

Related U.S. Application Data

(62) Division of application No. 11/487,254, filed on Jul. 13, 2006, now abandoned.

(51) Int. Cl.
*C12N 11/14* (2006.01)
*C12N 9/04* (2006.01)

(52) U.S. Cl. .................. 435/176; 977/714; 977/830; 435/190

(58) Field of Classification Search .................. 435/176, 435/190; 977/714, 830
See application file for complete search history.

(56) References Cited

U.S. PATENT DOCUMENTS

| 2004/0121018 | A1 | 6/2004 | Grate et al. |
| 2007/0077565 | A1 | 4/2007 | Kim et al. |
| 2007/0077566 | A1 | 4/2007 | Kim et al. |
| 2007/0077567 | A1 | 4/2007 | Kim et al. |
| 2007/0077568 | A1 | 4/2007 | Kim et al. |

FOREIGN PATENT DOCUMENTS

| EP | 1088887 A1 | 4/2001 |
| WO | 2006046865 A2 | 5/2006 |
| WO | 2006046865 A3 | 5/2006 |

OTHER PUBLICATIONS

Alavro et al., J. Phys. Chem B, May 2004, (7 pgs).
Bahr et al., J. Am. Chem. Soc., 2001, vol. 123, pp. 6536-6541.
Barton et al., Chem Rev. 2004, vol. 104, pp. 4867-4886.
Bullen et al., Biosensors & Bioelectronics, vol. 21, 2006, pp. 2015-2045.
Chen et al., J. Am. Chem. Soc., 2001, 123, pp. 3838-3839.
Heller et al., Phys. Chem. Chem. Phys., 2004, vol. 6, pp. 209-216.
Huang et al., Amer. Nano Letters, 2002, vol. 2, No. 4, pp. 311-314.

(Continued)

*Primary Examiner*—Karen Cochrane Carlson
*Assistant Examiner*—Rosanne Kosson
(74) *Attorney, Agent, or Firm*—James D. Matheson

(57) ABSTRACT

Disclosed is a composition and method for fabricating novel hybrid materials comprised of, e.g., carbon nanotubes (CNTs) and crosslinked enzyme clusters (CECs). In one method, enzyme-CNT hybrids are prepared by precipitation of enzymes which are subsequently crosslinked, yielding crosslinked enzyme clusters (CECs) on the surface of the CNTs. The CEC-enzyme-CNT hybrids exhibit high activity per unit area or mass as well as improved enzyme stability and longevity over hybrid materials known in the art. The CECs in the disclosed materials permit multilayer biocatalytic coatings to be applied to surfaces providing hybrid materials suitable for use in, e.g., biocatalytic applications and devices as described herein.

22 Claims, 5 Drawing Sheets

OTHER PUBLICATIONS

Jiang et al., J. Materials Chemistry, 2004, vol. 14, pp. 37-39.
Kam et al., J. Am. Chem. Soc., 2004, 126, pp. 6850-6851.
J.Kim et al., Biotechnology Advances, 24, 2006, pp. 296-308.
Lin et al., Nano Letters, vol. 0, No. ), A-E, 2003, (5 pgs).
G. Tayhas R. Palmore, Trends in Biotechnology, vol. 22, No. 3, Mar. 2004, pp. 99-100.
Peng et al., J. Am. Chem. Soc., 2003, vol. 125, pp. 15174-15182.
Rege et al., Nano Letters, 2003, vol. 3, No. 6, pp. 829-832.
Valentini et al., Anal. Chem., 2003, vol. 75, pp. 5413-5421.
Wong et al., Current Opinion in Biotechnology, 2003, vol. 14, pp. 590-596.
Kim et al., "Preparation of biocatalytic nanofibres with high active and stability via enzyme aggregate coating on polymer nanofibres," Nanotechnology 16:S382-388, 2005.
López-Serrano et al., "Cross-linked enzyme aggregates with enhanced activity: application to lipases," Biotechnology Letters 24:1379-1383, 2002.
Mateo et al., "A New, Mild Cross-linking Methodology to Prepare Cross-Linked Enzyme Aggregates," Biotechnology and Bioengineering 86(3):273-276, 2004.
Mateo et al., "Stabilisation of oxygen-labile nitrilases via co-aggregation with poly(ethyleneimine)," Journal of Molecular Catalysis B: Enzymatic 38:154-157, 2006.
Mateo et al., "Synthesis of enantiomerically pure (S)-mandelic acid using an oxynitrilase-nitrilase bienzymatic cascade: a nitrilase surprisingly shows nitrile hydratase activity," Tetrahedron: Asymmetry 17:320-323, 2006.
Schoevaart et al., "Preparation, Optimization, and Structures of Cross-Linked Enzyme Aggregates (CLEAs)," Biotechnology and Bioengineering 87(6):754-762, 2004.
Sheldon et al., "CLEAS: An effective technique for enzyme immobilization," Specialty Chemicals Magazine, pp. 40-42, Jul./Aug. 2003.
Sheldon et al., "Cross-linked enzyme aggregates (CLEAs): A novel and versatile method for enzyme immobilization (a review)," Biocatalysis and Biotransformation 23(3/4):141-147, 2005.
Sheldon et al., "Cross-linked enzyme aggregates (CLEAs)," Methods in Biotechnology 22. Immobilization of enzymes an cells (2nd ed.), Humana Press, Totowa, NJ, pp. 31-45, 2006.
Sheldon, "Immobilization of Enzymes as Cross-Linked Enzyme Aggregates: A Simple Method for Improving Performance," Biocatalysis in the Pharmaceutical and Biotechnology Industries, CRC Press, Taylor & Francis Group, Boca Raton, FL, pp. 351-362, 2006.
Sheldon et al., "Use of Cross-Linked Enzyme Aggregates (CLEAs) for performing biotransformations," Chemistry Today 25(1):62-67, 2007.
van Langen et al., "Penicillin Acylase Catalysed Synthesis of Ampicillin in Hydrophilic Organic Solvents," Adv. Synth. Catal., 345:797-807, 2003.
Kim Byoung Chang et al., Preparation of biocatalytic nanofibres with high activity and stability via enzyme aggregate coating on polymer nanofibres, Nanotechnology, Jul. 1, 2005, vol. 16, No. 7, Jul. 1, 2005.
Database Compendex [Online] Engineering Information, Inc., New York, NY, US; 2005, Kim Byoung Chan et al., stabilization in various nanostructured materials, XP002490317, Database accession No. E2006159816368 abstract.
Kim Jungbae et al., Challenges in biocatalysis for enzyme-based biofuel cells, Biotechnology Advances, vol. 24., No. 3, May 2006, pp. 296-308 (XP003490311).
Lee Jinwoo et al, Simple synthesis of hierarchically ordered mesocellular mesoporous silica materials hosting crosslinked enzyme aggregates, Small, Jul. 2005, vol. 1, No. 7, pp. 744-753 (XP002490312).
Lee Jinwoo et al, Preparation of a magnetically switchable bioelectrocatalytic system employing cross-linked enzyme aggregates in magnetic mesocellular carbon foam, Angew Chem Int. ED.; Angewandte Chemie-International Edition Dec. 1, 2005, vol. 44, No. 45, pp. 7427-7432 (XP002490314).
Lee Dohoon et al, Simple fabrication of a highly sensitive and fast glucose biosensor using enzymes immobilized in mesocellular carbon foam., Adv Mater; Advanced Materials, Dec. 5, 2005, vol. 17, No. 23, pp. 2828-2833 (XP002490313).
Jan U et al., Preparation of a highly stable, very active and high-yield multilayered assembly of glucose oxidase using carbohydrate-specific polyclonal antibodies, Biotechnology and Applied Biochemistry, Academic Press, US, vol. 39, No. Pt 2, Apr. 1, 2004, pp. 233-239, (XP008094646).
Wang J; Carbon-nanotube based ectrochemical biosensors: a review, Electroanalysis, vol. 17, No. 1, 2005, pp. 7-17, (XP002490315).
Fischback Michael B et al: Miniature biofuel cells with improved stability under continuous operation, Electroanalyis, vol. 18, No. 19-20, Oct. 2006, pp. 2016-2022, (XP002490316).
van Langen et al., "Cross-Linked Aggregates of (R)-Oxynitrilase: A Stable, Recyclable Biocatalyst for Enantioselective Hydrocyanation," Organic Letters 7(2):327-329, 2005.
Joshi et al, Anal. Chem. 2005, 77, pp. 3183-3188.
Liu et al, J. Phys. Chem. 2004, 108, pp. 8460-8466.

US 7,838,273 B2

BIOMOLECULAR HYBRID MATERIAL AND PROCESS FOR PREPARING SAME AND USES FOR SAME

CROSS REFERENCE TO RELATED APPLICATION

This application is a Divisional of U.S. application Ser. No. 11/487,254, filed on Jul. 13, 2006, now abandoned, published on Jan. 17, 2008 as Publication No. 2008/0014471 A1.

This invention was made with Government support under Contract DE-AC05-76RL01830 awarded by the U.S. Department of Energy. The Government has certain rights in the invention.

FIELD OF THE INVENTION

The present invention relates generally to a biomolecular hybrid material and a process for preparing same and uses for same. More particularly, the invention relates to an enzyme-carbon nanotube (CNT) hybrid material (enzyme-CNT hybrid) that is highly stable and exhibits high activity. The material finds use in bioelectronic and biochemical applications including, but not limited to, e.g., bioconversion, bioremediation, as well as devices including, but not limited to, e.g., biosensors, and biofuel cells.

BACKGROUND OF THE INVENTION

Hybrid materials combine various structural, functional, chemical, electronic, and/or other features suited to a desired application. Hybrid materials that include biomolecules (e.g., hybrid biomolecular materials or biomolecular hybrids) can provide features suited to bioelectronic applications. Of particular interest are biomolecular hybrid materials composed of carbon nanotubes (CNTs) given their useful properties. Enzyme-CNT hybrids, for example, are of special interest for biosensor and biofuel cell applications. In such applications, CNTs may be of various sizes, dimensions, and shapes. For example, CNTs may be single walled, double walled, and/or multiwalled, and/or be fashioned without limitation into ringed, straight, curled, or other structures. Depending on their structure, CNTs can further comprise, or be used in conjunction with, e.g., metals and/or semiconductors. CNTs are also strong structures and provide good thermal conductivity. Such characteristics have potential applications in nano-electronic and nano-mechanical devices, including, e.g., nano-wires, useful as components of electronic devices, e.g., field-effect transistors. While various strategies for fabricating enzyme-CNT hybrid materials have been reported in the art, short activity lifetimes of biocatalytic activity have hampered their practical implementation. Accordingly, new enzyme-CNT hybrids are needed that provide enzyme stabilization, longevity and high activity, promoting utility of such hybrids in a host of useful applications, including, e.g., bio-electrochemical applications.

SUMMARY OF THE INVENTION

In one aspect, a method is disclosed, comprising the steps: providing a material having a deposition surface(s); functionalizing the surface(s) yielding functional groups thereon operable for chemically attaching a seed enzyme(s) thereto; forming enzyme cluster(s); crosslinking the cluster(s) and attaching to the seed enzyme(s) forming cross-linked enzyme cluster(s) (CECs) on the surface forming a hybrid material, the CECs having a substantially stabilized enzyme activity; and whereby the CECs attached to the surface provide substantial enzyme activity per unit area or mass to the hybrid material.

In another aspect, a composition is disclosed, comprising: a material comprising a deposition surface(s) having functional groups chemically bound to a seed enzyme(s), wherein the seed enzyme(s) are chemically bound to CECs attached thereto and to the surface, wherein the CECs attached to the surface have a substantially stable enzyme activity; and whereby the CECs provide substantial enzyme activity per unit area or mass to the material.

In one embodiment, the material comprises a carbon nanotube(s).

In other embodiments, the CNT(s) have a cross-sectional diameter of from about 1 nm to about 100 nm; or, a cross-sectional diameter of greater than about 1 nm; or a cross-sectional diameter of less than about 100 nm.

In another embodiment, the CNT(s) have a length of from about 0.1 µm to about 100 µm.

In another embodiment, the CNT(s) are of a type selected from the group consisting of single-wall, double wall, multi-wall, straight, curved, ring, and combinations thereof.

In another embodiment, the material comprises a nanofiber(s).

In another embodiment, the material comprises a conductive nanowire(s).

In another embodiment, enzymes employed as seed enzymes or in preparation of CECs are selected from classes of enzymes in the group of oxidoreductases, transferases, hydrolases, lyases, isomerases, ligases, and combinations thereof.

In another embodiment, enzymes employed as seed enzymes or in preparation of CECs are selected from the group of chymotrypsin, trypsin, subtilisin, papain, lipases, horseradish peroxidase, soybean peroxidase, chloro peroxidase, manganese peroxidase, tyrosinase, laccase, dehalogenase, cellulase, glucosidase; xylanase, lactase, sucrase, organophosphohydrolase, cholinesterase, glucose oxidase, pyranose oxidase, alcohol dehydrogenase, glucose dehydrogenase, hydrogenase, glucose isomerase, nitroreductase, including combinations thereof.

In another embodiment, CECs attached to the surface of CNTs provide a coating to the hybrid material and an enzyme activity greater than provided by a monolayer of enzymes.

In another embodiment, the coating is a multilayer coating comprising of two or more layers of enzymes.

In another embodiment, the coating exhibits a resistance to proteolytic digestion greater than that of a material having a monolayer of enzymes covalently attached thereto.

In another embodiment, the enzyme activity of the coating is stable for greater than about 250 days in an aqueous buffer at room temperature.

In another embodiment, the enzyme activity and enzyme loading capacity of the coating is greater than for a monolayer of enzymes.

In another embodiment, the crosslinking is effected using a crosslinking agent selected from the group consisting of di-aldehydes, aldehydes, glutaraldehyde (GA), di-imides, 1-ethyl-3-dimethyl aminopropylcarbodiimide (EDC), di-isocyanates, isocyanates (—NCO), di-anhydrides, anhydrides, di-epoxides, epoxides, N-hydroxysuccinimide (NHS), and reagents having functional groups selected from aminyl (—NH), sulfhydryl (—SH), carbonyl (—C=O), carboxyl (—COOH), alcohols (—OH), silyl (e.g., bis(trimethoxysilyl), di-aldehydes, aldehydes (—CHO), di-imides, di-isocyanates, isocyanates (—NCO), di-anhydrides, anhydrides, di-epoxides, epoxides, aminyl (—NH), sulfhydryl (—SH), carbonyl (—C═O), carboxyl (—COOH), or the like, and combinations thereof.

In another embodiment, the forming of the enzyme cluster(s) comprises precipitation of enzyme(s) in the presence of the CNTs using a sufficient quantity of a precipitation reagent.

In another embodiment, a precipitation salt or precipitation reagent is selected from the group consisting of inorganic salts, organic solvents, polymers.

In one embodiment, inorganic salts are selected from ammonium sulfate ($NH_4SO_4$), potassium phosphate ($K_3PO_4$) and like salts.

In another embodiment, organic solvents are selected from alkanols, methanol, ethanol, 1-propanol, 2-propanol, t-butyl alcohol, acetone, acetonitrile, di-methyl-ether (DME), ethyl lactate, dimethylformamide (DMF), di-methyl-sulfoxide (DMSO).

In another embodiment, the polymer is polyethylene-glycol (PEG).

In another embodiment, CECs attached to a surface of the enzyme-CNT hybrid makes the hybrid functional in a catalytic application or device.

In another embodiment, the catalytic application or device is an electrochemical application or electrochemical device.

In another embodiment, the catalytic application or device is a biochemical application or biochemical device.

In another embodiment, the catalytic application or device is a biosensor application or biosensor device.

In another embodiment, the catalytic application or device is a biofuel cell application or biofuel cell device.

In another embodiment, the catalytic application or device is a lab-on-a-chip application or lab-on-a-chip device.

In another embodiment, the catalytic application or device is a protein digestion column application or protein digestion column device.

In another embodiment, the catalytic application or device is a bioremediation application or bioremediation device.

In another embodiment, the catalytic application or device is a bioconversion application or bioconversion device.

BRIEF DESCRIPTION OF THE DRAWINGS

A more complete appreciation of the invention will be readily obtained by reference to the following description of the accompanying drawing in which like numerals in different figures represent the same structures or elements.

FIGS. 1b-1d present SEM micrographs showing structures resulting from process steps presented in FIG. 1a.

DETAILED DESCRIPTION OF THE INVENTION

Figure 1A:
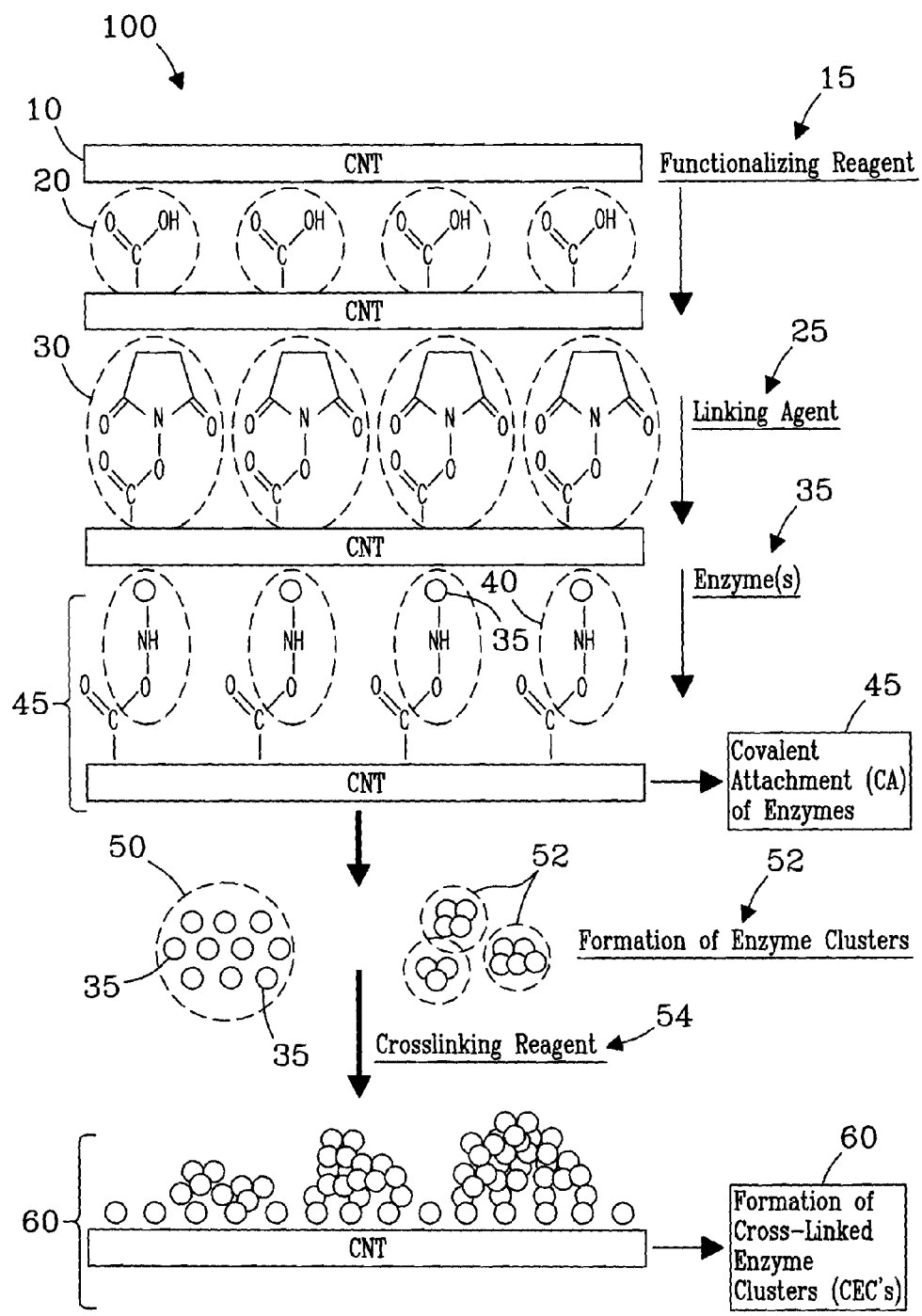
FIG. 1a illustrates a process for preparing highly stable and active enzyme-carbon nanotube hybrid materials, according to an embodiment of the invention.

The present invention relates generally to new hybrid materials and a process for preparing same and uses for same. Disclosed herein is an enzyme-CNT hybrid material characterized by high enzyme loading capacity, enzyme stability and longevity, and high enzyme activity per unit area or mass. Hybrid materials disclosed herein combine structural and electronic features of carbon nanotubes (CNTs) with functionality of biomolecules (e.g., enzymes) suited for use in bioelectronic and biochemical applications including, but not limited to, e.g., bioconversion, bioremediation, as well as devices including, but not limited to, e.g., biosensors, and biofuel cells. The term "carbon nanotubes" (CNTs) as used herein refers to thin cylinder-like structures comprised of carbon atoms having dimensions and/or diameters on a nanometer-scale. Hybrid materials described herein may further comprise, or be used in conjunction with, materials including, but not limited to, e.g., polymers, co-polymers, glasses, inorganics, ceramics, metals, composites, or combinations thereof. No limitations are intended.

The terms "linking reagent" and "linker" as used herein refer to reagents and/or compounds capable of chemically binding (i.e., "linking") two compounds together covalently, e.g., in conjunction with functional groups described further herein.

The term "cross-linking" as used herein refers to the process of chemically joining (covalently binding) two or more molecules by covalent bond between functional groups available and located on respective molecules being joined. Crosslinking reagents contain reactive ends to specific functional groups (e.g., primary amines, sulfhydryls, etc.) on proteins or other molecules. Cross-linking reagents include, but are not limited to, homobifunctional and heterobifunctional reagents. Homobifunctional cross-linking reagents have two identical functional (binding) groups for binding. Homobifunctional cross-linking reagents include, but are not limited to, e.g., di-aldehydes, di-isocyanates, di-anhydrides, di-epoxides, di-imides, or the like. A di-imide reagent such as 1-ethyl-3-dimethyl aminopropylcarbodiimide (EDC) is illustrative but not exclusive. EDC (1-ethyl-3-[3-dimethylaminopropyl]carbodiimide hydrochloride) promotes rapid preparation of peptide conjugates. Numerous chemical conjugates can be synthesized via available —COOH and —$NH_2$ groups; amide bond formed provides a neutral linkage ideal for preparing peptides and antigens. Heterobifunctional cross-linking reagents have two different functional (binding) groups that allow, e.g., sequential step-wise conjugations. Heterobifunctional reagents include, but are not limited to, e.g., amine-reactive N-hydro-succinimide-esters (e.g., NHS or sulfo-NHS reagents), sulfhydryl reagents, including, e.g., maleimides, pyridyl disulfides, and α-haloacetyls. No limitations are intended. Most widely-used heterobifunctional crosslinkers are those having an amine-reactive succinimidyl ester (i.e., NHS-ester) at one end and a sulfhydryl reactive group on the other end. The NHS-ester is less stable in aqueous solution and is usually reacted first in sequential crosslinking procedures. NHS-esters react with amines to form amide bonds. Carbodiimides (e.g., EDC) are zero-length crosslinkers and effect direct coupling between carboxylates (—COOH) and primary amines (—NH$_2$) and have been used in peptide synthesis, hapten-carrier protein conjugation, subunit studies and protein-protein conjugation. Additional cross-linking reagents include, e.g., glutaraldehyde [CAS No. 111-30-8], isocyanates (—NCO), anhydrides, epoxides, and reagents having functional groups selected from aldehydes (—CHO), aminyl (—NH), sulfhydryl (—SH), carbonyl (—C=O), carboxyl (—COOH), alcohols (—OH), silyl (e.g., bis(trimethoxysilyl)), isocyanates (—NCO), anhydrides, epoxides, sulfhydryl (—SH), carbonyl (—C=O), carboxyl (—COOH), or the like, and combinations thereof. All cross-linking reagents capable of binding enzymes and/or enzyme clusters to the surface of CNTs are within the scope of the disclosure.

Cross-linked enzyme cluster (CEC)-CNT hybrid materials described herein exhibit high enzymatic activity due to increased enzyme loading on the surface of CNTs. The following terms apply. "Initial enzyme activity" of an enzyme-CNT hybrid refers to the initial rate of product formation or compound depletion effected by the hybrid, measured at time t=0. "Residual enzyme activity" is defined as the enzyme activity or rate measured at a time other than t=0, using an identical concentration of enzyme and CNTs as for samples prepared at time t=0. "Relative activity" is defined as the ratio of the residual activity to initial activity. "Apparent activity" is defined as the initial enzyme activity of an enzyme-CNT hybrid per unit weight of CNTs in the sample. "Specific Activity" is defined as the enzyme activity per unit weight of enzyme employed. "High activity" means enzymatic activity greater than provided by a monolayer equivalent of covalently attached enzymes or enzyme clusters.

"Relative Sensitivity" is defined as the ratio of the sensitivity at each time point ($S_i$) to the initial sensitivity ($S_0$), i.e., ($S_i/S_0$).

"Power Density" as used herein in reference to biofuel cells is defined as the power output per unit geometric surface area of the enzyme anode. Stability of biofuel cell performance is assessed by obtaining power density as a function of time.

The term "coating" as used herein refers to a CNT surface covering comprised of enzymes and/or enzyme clusters.

The term "high loading" as used herein means an enzyme loading at other than that provided by a monolayer equivalent of enzymes.

The term "high stability" means no apparent loss in enzyme activity in an aqueous buffer solution (100 mM sodium phosphate, pH 7.0) at room temperature for a minimum of 250 days. Exceptional stability and high activity of CEC-CNT hybrid materials described herein improve performance in such applications as, e.g., biosensors and biofuel cells.

Preparation of CEC-CNT Hybrid Materials

FIG. 1a illustrates a generalized process 100 for preparing high activity enzyme-carbon nanotube hybrid materials, according to an embodiment of the invention. The hybrid is a multilayer material comprising cross-linked enzyme clusters (CECs) chemically attached to carbon nanotubes (CNT). Choice of enzymes is not limited. For example, enzymes used in conjunction with the invention are selected from enzyme classes including, but not limited to, e.g., oxidoreductases, transferases, hydrolases, lyases, isomerases, ligases, and combinations thereof. Representative enzymes include, but are not limited to, e.g., chymotrypsin, trypsin, subtilisin, papain, lipases, horseradish peroxidase, soybean peroxidase, chloroperoxidase, manganese peroxidase, tyrosinase, laccase, dehalogenase, cellulase, glucosidase, xylanase, lactase, sucrase, organophosphohydrolase, cholinesterase, glucose oxidase, pyranose oxidase, alcohol dehydrogenase, glucose dehydrogenase, hydrogenase, glucose isomerase, nitroreductase, or the like, and combinations thereof. No limitations are intended.

In an illustrative, but non-exclusive example, the process has been demonstrated using a well-characterized enzyme, e.g., glucose oxidase (GOx), yielding a CEC-GOx-CNT hybrid (also termed CEC-GOx hybrid). In the figure, carbon nanotube(s) (CNT) 10 is treated with a functionalizing reagent(s) 15 to functionalize the CNT(s) surface with functional groups 20 capable of chemically binding moieties and/or molecules of interest to the surface of the CNT(s). In the instant example, reagent(s) 15 for functionalizing CNT(s) 10 include protic acids (e.g., $H_2SO_4$, $HNO_3$, $H_3PO_4$, or combinations, e.g., $H_2SO_4/HNO_3$) yielding, e.g., carboxyl (—COOH) groups on the hybrid surface for chemically (e.g., covalently) binding other moieties thereto. No limitations are intended. All chemical reagents and reactions contemplated by those of skill in the art for functionalizing surfaces are within the scope of the disclosure.

Addition of a linking reagent(s) 25, e.g., EDC (1-[3-dimethylaminopropyl]-3-ethyl-carbodiimide hydrochloride or N-ethyl-N'-(3-dimethylaminopropyl) carbodiimide) and NHS(N-hydroxysuccinimide) (e.g., as EDC/NHS) to, e.g., the sample preparation solution, chemically binds the linking reagent(s) to functional groups 15 on the surface of CNT(s) 10. EDC catalyzes the formation of amide bonds between carboxylic acids or phosphates and amines by activating carboxyl or phosphate to form an O-urea derivative. N-Hydroxysuccinimide (NHS) is often used to assist coupling of the carbodiimide moiety of EDC. The derivative reacts readily with nucleophiles, i.e., electron-rich substituents or moieties. In the instant example, the coupling reaction linking the carboxylic group on the surface of the CNT(s) and the N-hydroxysuccinimide in the linking reagent(s) involves formation of an intermediate ester moiety 30. Linking reagent(s) can be used, e.g., to make ethers from alcohols; esters from acids, alcohols, or phenols; and peptide bonds from amines, as will be understood by those of skill in the art. Choice of linking agents depends at least in part on desired bond lengths, functional groups available for binding, as well as moieties to be attached on the surface of the CNT(s). No limitations are intended. All linking agents as will be contemplated by those of skill in the art are within the scope of the disclosure.

Enzymes 35 are chemically (i.e., covalently) attached to the surface of CNT(s) 10, e.g., via linking agents described herein, forming bond(s) 40 between, e.g., an amine (functional) group of the selected enzyme molecule (a nucleophile) and functional group(s) 15 on the CNT surface. However, the mode of binding is not intended to be limiting. Chemical attachment yields covalently attached (CA) enzyme "seeds" (also termed "seed enzymes" or "seed enzyme molecules") on the surface, forming the CA-GOx-CNT hybrid 45. In one illustrative but non-exclusive example, glucose oxidase (GOx) is selected as a representative enzyme. GOx enzymes 35 of the instant embodiment covalently attach to the alcohol moiety of the carboxyl functional group 15 on the surface of CNTs 10. The succinimide moiety of the ester 30 is replaced, leaving a GOx molecule covalently attached (CA) to the CNT via bond 40, forming a CA-GOx-CNT (or CA-GOx) hybrid (s) 45. Next, a quantity 50 of free (e.g., GOx) enzymes 35 is used to prepare enzyme clusters 52. Formation of enzyme clusters is effected by precipitation ("salting out") of free enzymes with a precipitation reagent (e.g., $NH_4SO_4$) as described herein. Subsequent treatment with a crosslinking reagent, e.g., glutaraldehyde (GA) 54, in the presence of previously prepared CA-GOx hybrids 45 crosslinks enzyme clusters and covalently binds them to the seed enzyme molecules of the CA-GOx-CNT hybrid, yielding multilayered cross-linked enzyme cluster (CEC)-CNT hybrid(s), i.e., CEC-GOx-CNT (or CEC-GOx) 60. The CEC-GOx-CNT hybrid comprises a coating of crosslinked enzyme clusters (CEC) attached to the surface of the CNTs.

Figure 1B:
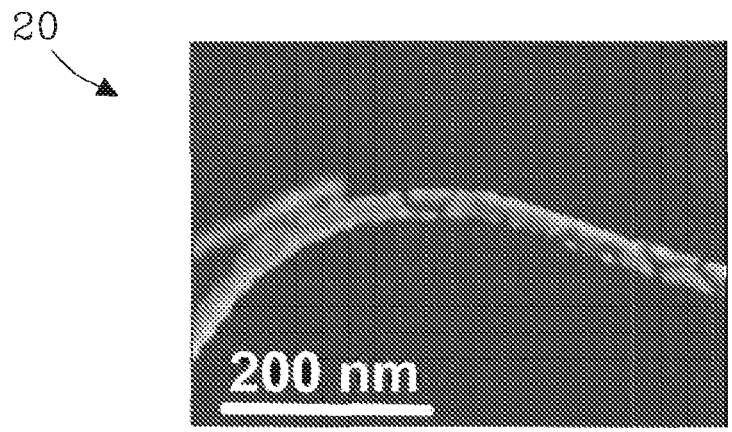
Figure 1C:
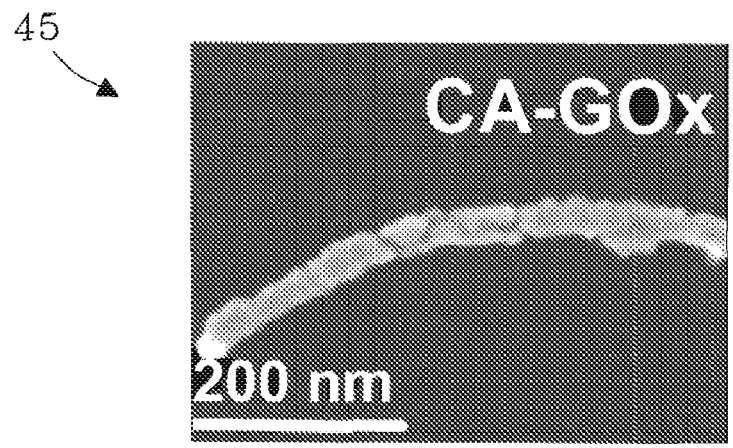
Figure 1D:
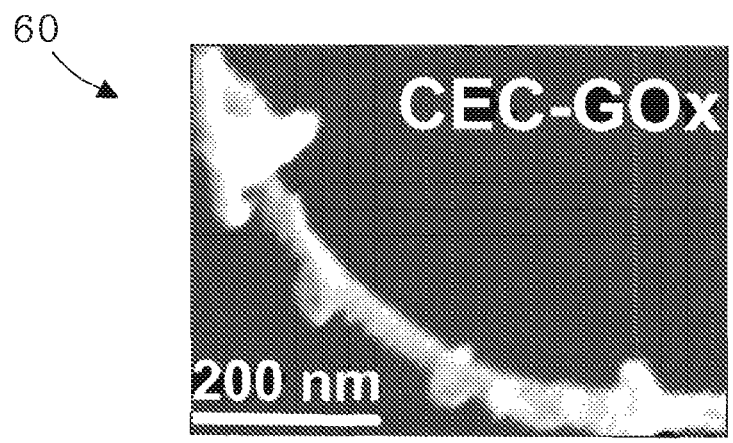

FIGS. 1b-1d present SEM micrographs (scale bar=200 nm) showing structures resulting from process steps illustrated in FIG. 1a, including, e.g., a functionalized CNT 20 (FIG. 1b), a CA-GOx-CNT (CA-GOx) hybrid 45 (FIG. 1c), and a CEC-GOx-CNT hybrid 60 (FIG. 1d). The CA-GOx hybrids 45 exhibit little difference in surface morphology compared to acid-treated CNTs 20 without enzyme(s). Since covalent attachment of enzyme "seeds" cannot develop more than a monolayer coverage of enzymes, enzyme (e.g., GOx) molecules attached in the CA-GOx hybrid (5.2×6.0×7.7 nm) 45 sample cannot be visualized at the SEM resolution. However, in contrast, cross-linked enzyme clusters (CEC) in the CEC-GOx-CNT hybrid 60 are easily observed on the surface of the CNT, indicating enzyme loading is much greater than that of the CA-GOx hybrid, due principally to multilayers of cross-linked enzyme clusters in the CEC-GOx-CNT hybrid 60.

Activity

Figure 2A:
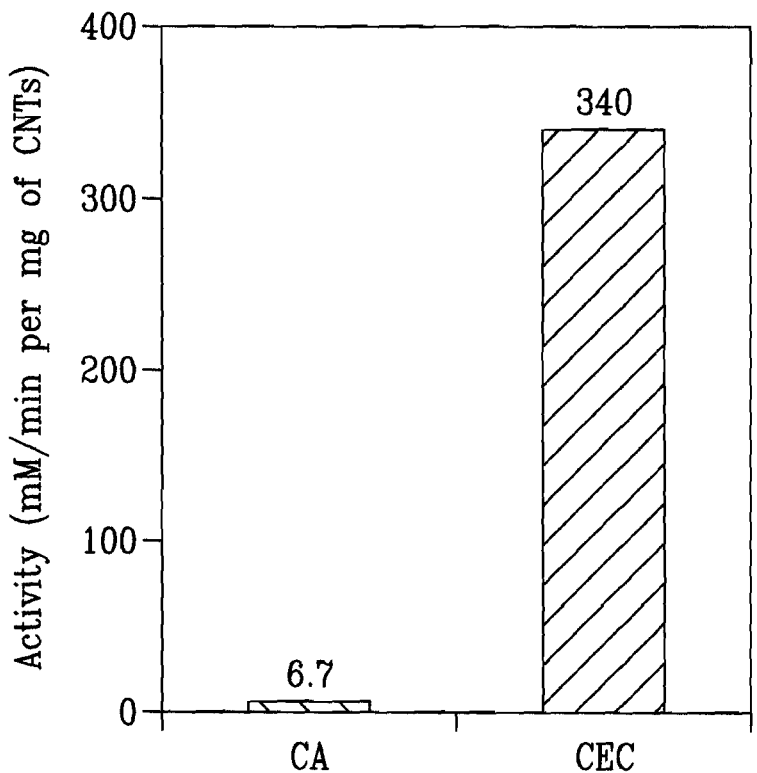
FIG. 2a is a plot of initial activity of a CEC-GOx-CNT hybrid material compared to a CA-GOx-CNT control, according to an embodiment of the invention.

Initial activities of CEC-GOx and CA-GOx hybrid (control) samples were measured. FIG. 2a shows the apparent activity of CEC-GOx hybrids compared to the CA-GOx control. Apparent activities for CA-GOx and CEC-GOx hybrids were 6.7 mM·min$^1$ per mg of CNTs and 340 mM·min$^{-1}$ per mg of CNTs, respectively. The CEC-GOx hybrids showed a 50 times greater apparent activity than the control due to multilayered CECs on the latter hybrid. Enhanced activity observed for the CEC-GOx hybrids is expected to significantly improve performance of these and similar hybrid-CNT materials in various applications and devices, including, e.g., biosensors and biofuel cells.

Stability

Figure 2B:
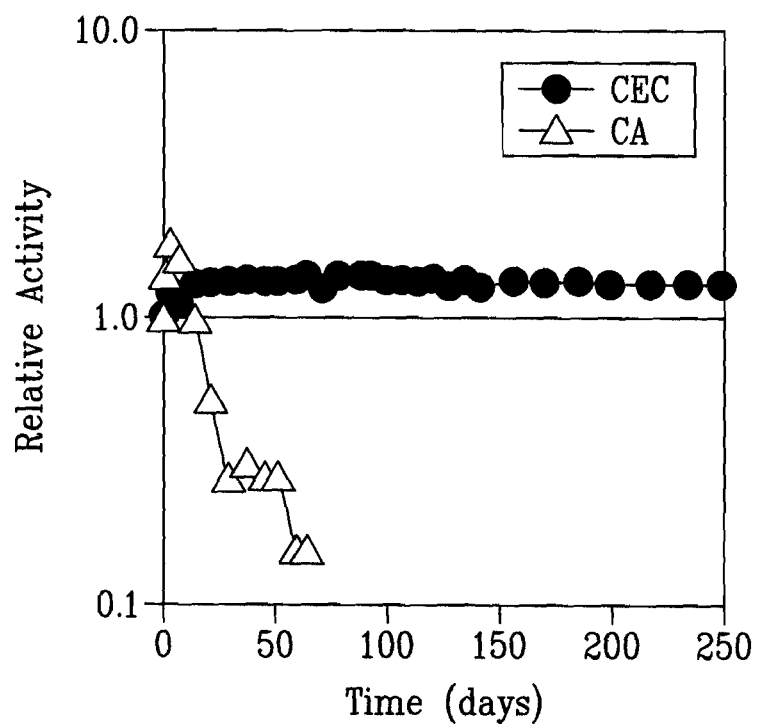
FIG. 2b is a plot showing stability of a CEC-GOx-CNT hybrid material compared to a control, according to an embodiment of the invention.

FIG. 2b compares relative activity, a measure of stability, of a CA-GOx (control) hybrid and CEC-GOx hybrid at room temperature. CA-GOx hybrids exhibit a continuous decline in activity and ultimate deactivation while CEC-GOx hybrids exhibit no apparent loss in activity over a period of greater than 250 consecutive days. Results demonstrate that multi-point (covalent) attachment of cross-linked enzyme clusters (CECS) prevents enzyme molecules in the CEC-GOx hybrid samples from structural denaturation and leaching, leading to no apparent deactivation of the GOx activity for more than 250 days.

Bioelectrochemical Application (I. Biosensor)

Suitability of CEC-GOx-CNT hybrid materials as highly stable and active enzyme systems has been demonstrated for bioelectrochemical applications. Electrodes comprising the CEC-GOx-CNT hybrid materials were tested against a CA-GOx-CNT (control), described further herein. Performance was evaluated in two specific applications: (i) as a biosensor for glucose sensing and (ii) in a biofuel cell. Applications are not intended to be limiting.

Figure 3:
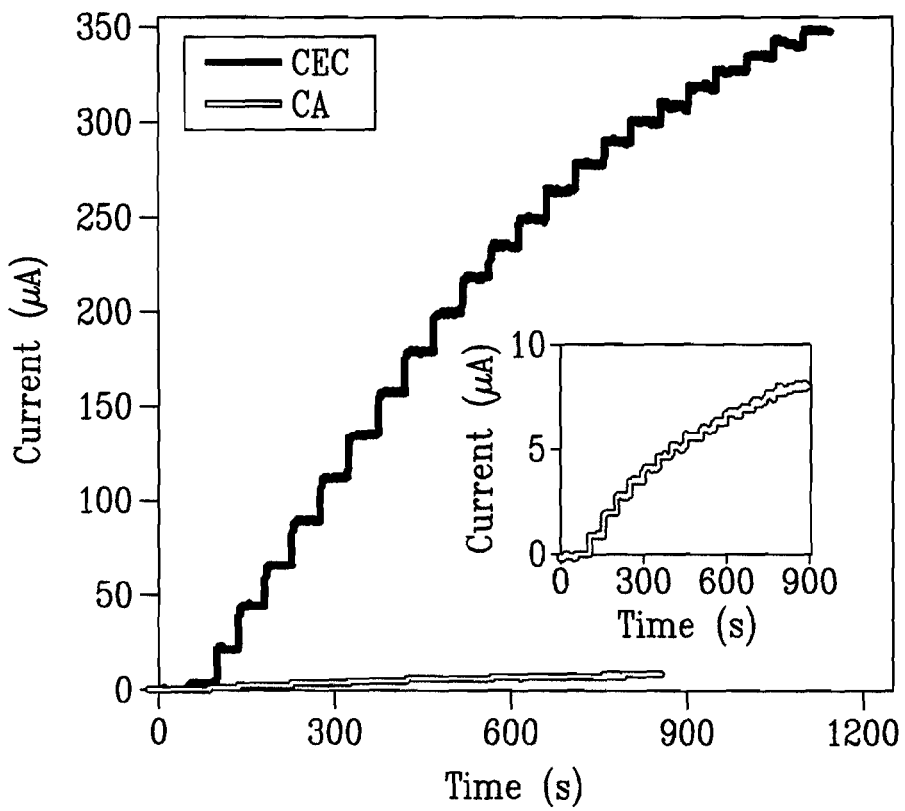
FIG. 3 is a plot showing current response upon addition of glucose for electrodes comprising a CEC-GOx-CNT hybrid material configured for use as a glucose biosensor, according to an embodiment of the invention.

FIG. 3 is a plot showing current response upon addition of glucose (i.e., increase of 1 mM glucose per injection) for working electrodes prepared with CEC-GOx hybrid materials used as glucose biosensors compared to a CA-GOx (control). Detection sensitivity was obtained from the slope of current increase to the glucose concentration. Sensitivities of the CEC-GOx hybrid electrodes and the CA-GOx (control) electrodes were ($2.3 \times 10^{-3}$ A·M$^{-1}$·cm$^{-2}$) and ($0.8 \times 10^{-3}$ A·M$^{-1}$ cm$^{-2}$), respectively, representing about 3 times greater sensitivity for the CEC-GOx hybrid material to the control. Detection limits for the CEC-GOx hybrid electrode and the CA-GOx (control) electrode were 0.03 mM and 0.07 mM, respectively, indicating about 2.3 times lower detection limit with the CEC-GOx hybrid. Better sensitivity and lower detection limits for the CEC-GOx hybrid electrode is attributed to its greater enzyme loading.

Figure 4:
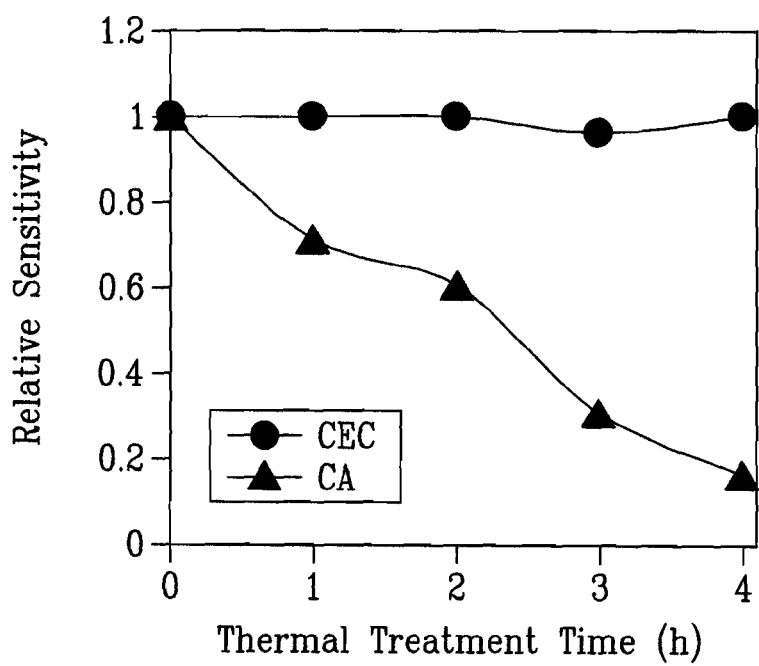
FIG. 4 is a plot showing stability of sensitivity for electrodes comprising a CEC-GOx-CNT hybrid material following thermal treatment at 50° C. compared to a CA-GOx-CNT control, according to an embodiment of the invention.

Stability of electrode performance for glucose sensing was tested by measuring sensitivity after thermal treatment at 50° C. as a function of time. FIG. 4 is a plot of the relative sensitivity for electrodes prepared with a CEC-GOx-CNT hybrid material compared to a CA-GOx-CNT (control). Sensitivity of the CA-GOx-CNT electrode was reduced by more than 80% after four-hour thermal treatment, while the CEC-GOx-CNT electrode showed negligible decrease in sensitivity after thermal treatment under identical conditions.

Bioelectrochemical Application (II. Biofuel Cell)

Figure 5:
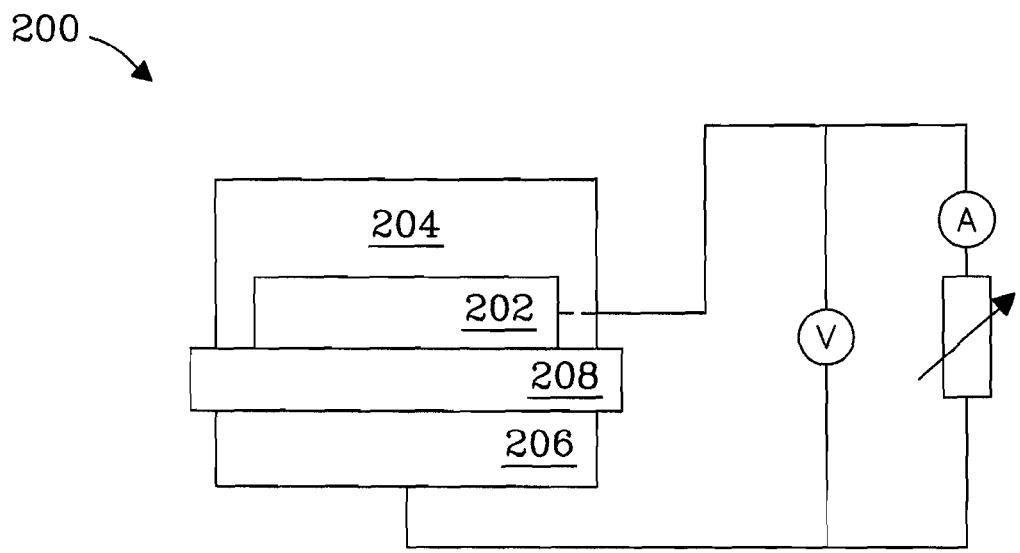
FIG. 5 is a schematic of a biofuel cell configured with an enzyme electrode (anode) comprised of a CEC-GOx-CNT hybrid material, according to an embodiment of the invention.

FIG. 5 is a schematic of a biofuel cell 200 of a simple test configuration, configured with an electrode comprised of a CEC-GOx-CNT hybrid material, detailed further in Example 8. The biofuel cell includes a fuel chamber 204 for holding fuel, e.g., glucose. Internal to the chamber is an enzyme anode (electrode) 202 comprised of a CEC-GOx-CNT (CEC-GOx) hybrid material, which was tested against a CA-GOx-CNT (CA-GOx) hybrid control. The enzyme anode is prepared by immobilizing enzymes (e.g., GOx) onto CNTs, e.g., as CEC-enzyme-CNT hybrids (e.g., CEC-GOx-CNT); dispersing the hybrid material into a Nafion® solution; immersing a backing material [e.g., carbon paper (Toray® paper), carbon felt, or carbon cloth] into the resulting Nafion® solution containing the CEC-GOx-CNT hybrids for ~10 minutes; allowing the immersed backing material to dry. The biofuel cell further includes a membrane cathode electrode assembly (MCEA) available commercially (Fuel cell Store, Boulder, Colo., USA) that includes a cathode 206 and proton exchange membrane 208 comprised of Nafion®. In the instant embodiment, the cathode is a platinum-containing membrane, but is not limited thereto. The proton exchange membrane 208 is positioned between fuel chamber 204 and cathode 206. Components are electrically connected, generating a power output when put under a specific application load.

Figure 6:
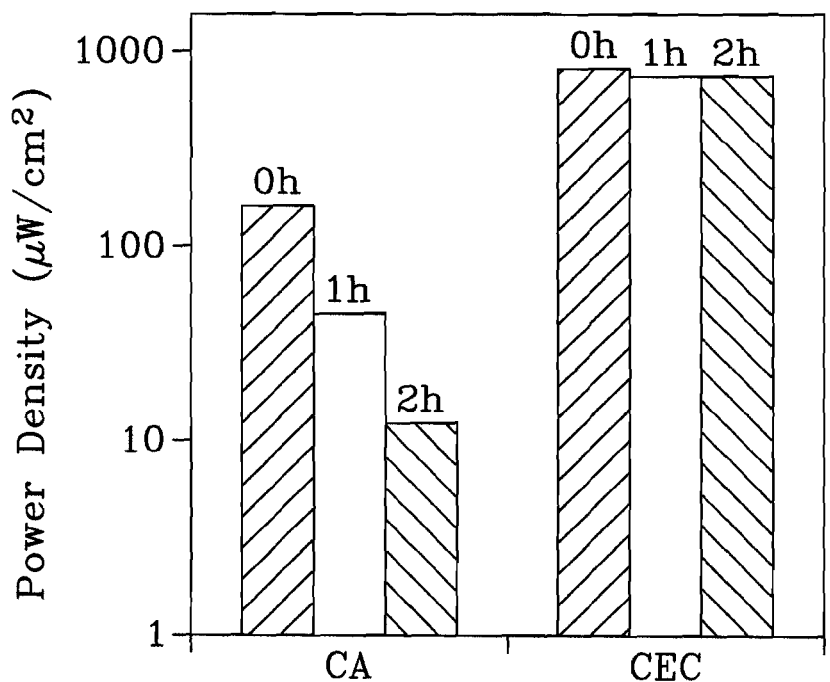
FIG. 6 compares power density outputs for a biofuel cell configured with an enzyme anode comprised of a CEC-GOx-CNT hybrid material compared to a control, according to an embodiment of the invention.

FIG. 6 presents power densities for biofuel cells prepared as described with reference to FIG. 5. Biofuel cells were configured with enzyme anodes (electrodes) prepared from CEC-GOx and CA-GOx (control) hybrid materials, respectively. Stability of biofuel cell performance was determined by measuring the maximum power density at about 300 mV following incubation of the enzyme anodes (electrodes) in aqueous buffer at 50° C. over time. As illustrated in FIG. 6, initial power densities of biofuel cells prepared using CEC-GOx electrodes and CA-GOx (control) hybrid electrodes were 810 µW·cm$^{-2}$ and 161 µW·cm$^{-2}$, respectively. Results show the power density (power output) of the biofuel cell configured with a CA-GOx-CNT (control) electrode was reduced by 92% after a two-hour incubation of the enzyme anode at 50° C., while the biofuel cell configured with a CEC-GOx-CNT hybrid electrode showed a power density decrease of less than 10% under the same thermal treatment. The CEC-GOx-CNT anode showed no apparent (observed) decrease in power density even after incubation in aqueous buffer solution at room temperature for 86 days. Residual power density of the CEC-GOx electrode was 60 times greater than that observed for the CA-GOx electrode following a 2 h thermal treatment at 50° C. Results further indicate that the CEC-GOx-CNT hybrid electrode improves biofuel cell performance by at least a factor of five (5) compared to the control, even though the apparent activity of CEC-GOx is about 50 times greater than that of the CA-GOx (FIG. 2a). Power output of a biofuel cell is governed not only by the enzyme activity, but also by factors including, but not limited to, e.g., mass transfer rate, electron transfer rate, and internal resistances. Improved enzyme stability demonstrated for the CEC-GOx-CNT hybrid system of the present invention can help overcome the short performance lifetimes, a limitation to practical application of biofuel cells known in the art. The excellent stability of power output (0.81 mW·cm$^{-2}$) opens up a new potential for the practical application of enzyme-based biofuel cells.

The following examples are intended to promote a further understanding of the present invention. Example 1 describes preparation of CEC-enzyme-CNT hybrid materials of the invention. Example 2 compares activity of CEC-enzyme-CNT hybrid materials. Example 3 compares stability of CEC-enzyme-CNT hybrid materials. Example 4 describes importance of precipitation step in preparation of CEC-enzyme-CNT hybrid materials. Example 5 details preparation of enzyme electrodes prepared from CEC-enzyme-CNT hybrid materials. Example 6 demonstrates utility of CEC-enzyme-CNT hybrid materials of the invention in enzyme electrodes for electrochemical measurements, e.g., for glucose sensing. Example 7 describes thermal stability of CEC-enzyme-CNT hybrid materials of the invention. Example 8 describes preparation of CEC-enzyme-CNT hybrid material electrodes for uses in a biofuel cell. Example 9 describes a biofuel cell configured with a CEC-enzyme-CNT hybrid material of the invention suitable for biofuel cell applications. Example 10 details stability of CEC-enzyme-CNT hybrid material electrodes deployed in biofuel cells.

EXAMPLE 1

Preparation of CEC-CNT (e.g., CEC-GOx-CNT) Hybrid Materials

CNTs (multi-walled, 30±15 nm O.D. and 1~5 μm in length, purity>95%) were obtained commercially (Nanolab, Inc., Watertown, Mass., USA) and treated with acids prior to use. In a typical preparation, 100 mg of CNT powder was added to acid solution consisting of $H_2SO_4$ (98%, 7.5 mL) and $HNO_3$ (70%, 2.5 mL), followed by incubation overnight at room temperature under shaking conditions (200 rpm). Acid-treated CNTs were washed with distilled water and dried at 80° C. in a vacuum oven. For surface functionalization, acid-treated CNTs (~20 mg) were first suspended in distilled water (10 mL) and then mixed with 4 mL of 2-Morpholinoethanesulfonic acid (MES) buffer (pH 6.5; 500 mM), 4 mL of N-Hydroxysulfosuccinimide (NHS) aqueous solution (434 mM), and 2 mL of N-ethyl-N'-(3-dimethylaminopropyl) carbodiimide hydrochloride (EDC) aqueous solution (53.2 mM). After vigorous stirring at room temperature for 1 h, the suspension was centrifuged and washed with 100 mM MES buffer (pH 6.5). Covalent attachment of enzymes to the CNT surface was achieved by mixing 2 mL of the suspension of functionalized CNTs (1 mg·mL$^{-1}$) with 1 mL of GOx (10 mg·mL$^{-1}$) and allowed to react for ~1 h at room temperature under shaking conditions (200 rpm). CA-GOx (CNT hybrid) samples were prepared by adding 2 mL of sodium phosphate buffer (pH 7.0, 100 mM) and incubated overnight at 4° C. CEC-GOx samples were prepared by mixing 2 mL of ammonium sulfate solution (550 mg·ml$^{-1}$) (for 30 min under shaking conditions at 200 rpm) with the suspension solution to precipitate GOx in the vicinity of the CNTs. Then, GA solution (0.5 wt %) was used to crosslink GOx molecules in the enzyme precipitates entangled with CNTs. After addition of GA, the suspension was first shaken (200 rpm) at room temperature for 30 min and then incubated overnight at 4° C. Preparations were treated with 100 mM Tris buffer (pH 7.4) to cap unreacted aldehyde groups, and washed with 100 mM sodium phosphate buffer (pH 7.0) until no enzymes were detected in the washing solution. All GOx-CNTs (i.e., CA-GOx-CNTs and CEC-GOx-CNTs) were then re-dispersed into 100 mM sodium phosphate buffer (pH 7.0) at a CNT concentration of 0.5 mg·mL$^{-1}$.

EXAMPLE 2

Activity of CEC-enzyme-CNT Hybrid Materials (CEC-GOx-CNT vs. Control)

Initial activities of both CA-GOx and CEC-GOx CNT hybrid samples prepared in aqueous buffer solution (100 mM sodium phosphate, pH 7.0) at room temperature were measured using a conventional GOx assay described, e.g., by H. U. Bergmeyer, et al. ("Methods of Enzymatic Analysis", pp. 457-458, Academic Press Inc., New York, N.Y., 1974). In air-saturated solution, GOx-catalyzed oxidation of glucose produced hydrogen peroxide, which reacted with o-dianisidine in the presence of peroxidase. Concentration of oxidation product was monitored by absorbance at a wavelength of 500 nm. Initial activities were converted to apparent activities (activity per unit weight of CNTs) to reflect enzyme loading for determining practical performance in electrochemical and/or bioelectrochemical applications.

EXAMPLE 3

Thermal Stability of CEC-Enzyme-CNT Hybrid Materials (CEC-GOx-CNT vs. Control)

Stability of immobilized enzymes of CEC-GOx and CA-GOx (control) hybrids was determined by measuring residual GOx activity as a function of incubation time. Samples (0.05 mg·mL$^{-1}$) were incubated at room temperature. At each time point, a small aliquot was taken for the measurement of residual activity. Relative activity was calculated as the ratio of residual activity to initial activity of each sample for easy comparison of stability results. CA-GOx (control) samples showed a continuous deactivation while CEC-GOx samples exhibited substantially no activity loss over about 250 consecutive days. Results indicate that multi-point covalent crosslinking of enzyme molecules effectively protects the enzyme molecules in the CECs from structural denaturation.

EXAMPLE 4

Precipitation of Enzymes

A sample of CA-GOx-CNT hybrids was subjected to gluteraldehyde (GA) treatment of the enzyme solution without any precipitation of GOx enzymes as enzyme clusters. Apparent activity of this hybrid sample (without precipitation) was 6.9 mM·min$^{-1}$ per mg of CNTs, which is much lower than that of CEC-GOx-CNT hybrid (338 mM·min$^{-1}$ per mg of CNTs) and similar to that of CA-GOx-CNT (control) hybrid (6.7 mM·min$^{-1}$ per mg of CNTs). Stability of this hybrid sample (without precipitation) results in a rigorous inactivation, similar to the inactivation observed for the CA-GOx-CNT hybrid described previously. Results suggest the importance of precipitation for preparing highly active and stable CEC-CNT hybrid materials.

EXAMPLE 5

Electrodes Prepared from CEC-CNT Hybrids for Use in a Glucose Sensing Biosensor

Enzyme electrodes were prepared by entrapping respective CA-GOx-CNT (CA-GOx) or CEC-GOx-CNT (CEC-GOx) hybrids in a sulfonated tetrafluoroethylene copolymer also known as Nafion® (DuPont, Wilmington, Del., USA) having suitable permeation selectivity and biocompatibility, as follows. ~2 mg·mL$^{-1}$ of CA-GOx (control) or CEC-GOx hybrid materials were dispersed in respective ~100 mM sodium phosphate buffer solution (pH 7.0) containing approximately 0.5 wt % Nafion® (DuPont, Wilmington, Del., USA), yielding a Nafion® suspension. Electrodes for glucose sensing were fabricated on 3 mm diameter glassy carbon electrodes (GCE) available commercially (CH Instruments Inc., Austin, Tex., USA). ~20 µL of Nafion® suspension was cast on the polished electrode surfaces and allowed to dry for two hours at ambient conditions, readying the enzyme electrodes for use as a standalone working electrode. Biosensor measurements are described in Example 5 hereafter.

EXAMPLE 6

Electrochemical (Glucose Sensing) Measurements

Cyclic voltammetry experiments were performed using a three-electrode electrochemical cell. CA-GOx (control) and CEC-GOx hybrid electrodes were prepared as in Example 5 as respective working electrodes, with standard Ag/AgCl electrodes and platinum wires used as reference and counter electrodes, respectively. ~10 mL of a (100 mM) phosphate buffer solution containing ~0.5 mM benzoquinone as a redox mediator was added to the cell as electrolyte. For the amperometry study, potential of the working electrode was fixed at 140 mV vs. the Ag/AgCl reference electrode. Current response as a function of change in glucose concentration was measured in the gently-stirred buffer solution used. Small aliquots (~5 µl) of glucose stock solution (2 M, in 100 mM phosphate buffer at pH 7.0) were added at a typical time interval of 60 s. Each aliquot addition increased the glucose concentration by 1 mM at successive additions of glucose aliquots. Glucose concentration was measured over a dynamic range for both electrodes of up to about 10 mM glucose. Detection limits of the CA-GOx and CEC-GOx electrodes were about 0.07 mM and 0.03 mM, respectively, based on a signal-to-noise ratio of 3.

EXAMPLE 7

Thermal Stability Measurements of Enzyme-CNT Hybrid Electrodes

Thermal stability of the enzyme (e.g., biosensing) electrodes prepared as in Example 5 was assessed by collecting amperometric measurements after ~2 h incubation in a ~100 mM phosphate buffer (pH 7.0) at 50° C. Sensitivity of the CA-GOx (control) enzyme electrodes was reduced by more than 80% after a four-hour thermal treatment, while the CEC-GOx enzyme electrodes showed negligible decrease in sensitivity after thermal treatment under identical conditions.

EXAMPLE 8

Preparation of CEC-Enzyme-CNT Hybrid Electrodes for Use in a Biofuel Cell

Enzyme electrodes were prepared using respective CEC-GOx-CNT or CA-GOx-CNT (control) hybrid materials and configured for use in a biofuel cell as follows. A ~370 µm thick carbon composite paper, also known as Toray® paper, available commercially (Fuel Cell Store, Boulder, Colo., USA) was used as an electrode backing material. A suspension was prepared by dispersing and entrapping ~3 mg·mL$^{-1}$ CA-GOx (control) or CEC-GOx hybrid material into a buffer solution containing ~0.5 wt % Nafion® (DuPont, Wilmington, Del., USA) as described in Example 4. A piece of Toray® paper (geometric surface area ~0.33 cm$^2$) was immersed in the suspension for 10 min and subsequently dried overnight at ambient conditions integrating the CA-GOx (control) or CEC-GOx-CNT hybrid enzyme electrodes (e.g., enzyme anode). Resulting electrodes were washed and stored in (100 mM) phosphate buffer at room temperature until use.

EXAMPLE 9

Biofuel Cell Configured with CEC-enzyme-CNT Hybrid Material

A biofuel cell consisting of a fuel chamber, an enzyme anode, and a commercially available membrane cathode electrode assembly (MCEA) (Fuel Cell Store, Boulder, Colo., USA), described herein. The enzyme anode and the proton exchange membrane of the MCEA were positioned between the fuel chamber and the cathode membrane in the assembled biofuel cell, with the anode and cathode connected electrically. The cathode of the MCEA is a gas diffusion-membrane having a platinum (Pt) loading of about 4 mg cm$^2$. In typical operation, a phosphate buffer solution (100 mM, pH 7.0) containing 200 mM D(+) glucose and (10 mM) benzoquinone, a redox mediator, was placed in the fuel chamber as a fuel. Characteristic voltage and current curves were obtained using a multimeter (e.g., a Keithley 2700 digital multimeter, Keithley, Ohio, USA). Current and power densities were calculated based on geometrical surface area of the electrode. Electrodes were stored at room temperature in a (100 mM) phosphate buffer (at pH 7.0) prior to use.

EXAMPLE 10

Stability of Enzyme-CNT Hybrid Electrodes Deployed in Biofuel Cells Configured with Same Enzyme stability of CNT hybrid materials in a test Biofuel Cell configuration has been demonstrated using enzyme electrodes prepared as described in Example 8 from respective CA-GOx (control) and CEC-GOx CNT hybrid materials. Stability of the biofuel cell performance was determined by measuring power density for respective CA-GOx (control) and CEC-GOx hybrid enzyme electrodes over a ~2 h incubation period in aqueous buffer at 50° C. Initial power densities (time t=0) for CA-GOx (control) and CEC-GOx biofuel cells were 161 and 810 µW·cm$^{-2}$, respectively. Power density of the CA-GOx electrode biofuel cell was reduced by 92% after a two-hour incubation period while the CEC-GOx electrode and biofuel cell showed less than a 10% decrease in power density under identical conditions. Following two-hour thermal treatment at 50° C., residual power densities of the CEC-GOx electrode and the CA-GOx (control) electrode were 737 and 12 µW·cm$^{-2}$, respectively, representing 60 times greater power density for the CEC-GOx electrode. The excellent stability of the CEC-GOx-CNT electrode system shows suitability of the present invention for new and practical applications including, e.g., enzyme-based biofuel cells.

CONCLUSIONS

In summary, a unique hybrid material consisting of enzymes and conductive CNTs was developed and examined for bioelectrochemical applications. The high activity and exceptional stability of this hybrid material will provide new opportunities in the development of practical and sustainable devices. Although the current work is mainly focused on the fabrication of GOx coating, the protocol described in this paper can be applied to other enzymes and proteins for generation of a wide spectrum of novel bioactive materials.

The new approach of enzyme cluster coatings on conductive CNTs yields high activity/high stability hybrid materials and substrates, useful in new biocatalytic immobilized enzyme systems with potential applications in bioconversion, bioremediation, biofuel cells, and biosensors. As will be appreciated by those of skill in the art, many and varied systems and processes may be employed for manufacture of both CNTs upon which enzymes will be attached. Thus, all processes and/or systems as will be contemplated by those of skill in the art for using CNTs in conjunction with enzyme cluster coatings are within the scope of the invention. No limitations are intended.

While the preferred embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

I claim:

1. A method for preparing a biomolecular hybrid material, comprising the steps of:
   (a) chemically attaching one or more seed enzymes to the surface of a carbon nanotube (CNT) to immobilize said enzyme or enzymes on said CNT;
   (b) forming one or more enzymes into clusters by crosslinking said enzymes with a crosslinking agent in solution, thereby forming crosslinked enzyme clusters (CECs);
   (c) precipitating said CECs from said solution to isolate said CECs; and
   (d) chemically attaching said CECs to said seed enzymes by contacting said CECs and said immobilized seed enzymes with said crosslinking agent, wherein said CECs have a thickness that provides an enzyme activity that is greater than the activity of the same one or more enzymes in the CECs in a monolayer configuration on said surface of said CNT.

2. The method of claim 1, wherein said CNT has a cross-sectional diameter of from about 1 nm to about 100 nm.

3. The method of claim 1, wherein said CNT has a cross-sectional diameter of greater than 1 nm.

4. The method of claim 1, wherein said CNT has a cross-sectional diameter of less than 100 nm.

5. The method of claim 1, wherein said CNT has a length of from about 0.1 µm to about 100 µm.

6. The method of claim 1, wherein said CNT is selected from the group consisting of single-walled CNTs, double-walled CNTs, multiple walled CNTs, straight CNTs, curved CNTs, ring shaped CNTs, and combinations thereof.

7. The method of claim 1, wherein said one or more preselected seed enzymes are selected from the group consisting of oxidoreductases, transferases, hydrolases, lyases, isomerases, ligases, and combinations thereof.

8. The method of claim 1, wherein said one or more preselected seed enzymes are selected from the group consisting of chymotrypsin, trypsin, subtilisin, papain, lipases, horseradish peroxidase, soybean peroxidase, chloroperoxidase, manganese peroxidase, tyrosinase, laccase, dehalogenase, cellulase, glucosidase, xylanase, lactase, sucrase, organophosphohydrolase, cholinesterase, glucose oxidase, pyranose oxidase, alcohol dehydrogenase, glucose dehydrogenase, hydrogenase, glucose isomerase, nitroreductase, and combinations thereof.

9. The method of claim 1, wherein said chemically attached CECs are comprised of two or more layers of enzymes.

10. The method of claim 1, wherein said enzyme activity of said biomolecular hybrid material has a duration of greater than 250 days as measured in an aqueous buffer at room temperature without measurable loss in activity.

11. The method of claim 1, wherein crosslinking of said CECs is performed using a crosslinking agent selected from the group consisting of: di-aldehydes, aldehydes, glutaraldehyde (GA), di-imides, 1-ethyl-3-dimethyl aminopropylcarbodiimide (EDC), di-isocyanates, isocyanates (—NCO), di-anhydrides, anhydrides, di-epoxides, epoxides, N-hydroxysuccinimide (NHS), and reagents having functional groups selected from aminyl (—NH), sulfhydryl (—SH), carbonyl (—C═O), carboxyl (—COOH), alcohols (—OH), silyl, bis(trimethoxysilyl, di-aldehydes, aldehydes (—CHO), di-imides, di-isocyanates, isocyanates (—NCO), di-anhydrides, anhydrides, di-epoxides, epoxides, aminyl (—NH), sulfhydryl (—SH), carbonyl (—C═O), carboxyl (—COOH), and combinations thereof.

12. The method of claim 1, wherein said CECs are precipitated from solution by adding a precipitation reagent to said solution.

13. The method of claim 12, wherein said precipitation reagent is an inorganic salt.

14. The method of claim 13, wherein said inorganic salt is selected the group consisting of ammonium sulfate, potassium phosphate, and combinations thereof.

15. The method of claim 12, wherein said precipitation reagent is selected from the group consisting of alkanols, acetone, acetonitrile, di-methyl-ether, ethyl lactate, dimethylformamide, di-methyl-sulfoxide, and combinations thereof.

16. The method of claim 13, wherein said precipitation reagent is polyethylene-glycol.

17. The method of claim 1, wherein said biomolecular hybrid material is a part of a device.

18. The method of claim 17, wherein said device is a biocatalytic device.

19. The method of claim 1, wherein said CECs comprise enzymes selected from the group consisting of oxidoreductases, transferases, hydrolases, lyases, isomerases, ligases, and combinations thereof.

20. The method of claim 1, wherein said CECs include enzymes selected from the group consisting of chymotrypsin, trypsin, subtilisin, papain, lipases, horseradish peroxidase, soybean peroxidase, chloroperoxidase, manganese peroxidase, tyrosinase, dehalogenase, cellulose, glucosidase, xylanase, lactase, sucrase, organophosphohydrolase, cholinesterase, glucose oxidase, pyranose oxidase, alcohol dehydrogenase, glucose dehydrogenase, hydrogenase, glucose isomerase, nitroreductase, and combinations thereof.

21. A method for preparing a biomolecular hybrid material, comprising the steps of:
   (a) functionalizing a surface of a carbon nanotube (CNT) to obtain attachment sites thereon;
   (b) chemically attaching a seed enzyme to one or more of said attachment sites to obtain chemically attached seed enzymes on said surface of said CNT;
   (c) forming enzyme clusters by incubating said enzyme with a crosslinking agent in solution, each cluster having a plurality of interconnected crosslinked enzymes, thereby forming crosslinked enzyme clusters (CECs);
   (d) precipitating said CECs from said solution to isolate said CECs; and
   (e) chemically attaching said CECs to one or more of said seed enzymes by contacting said CECs and said seed enzymes with said crosslinking agent, wherein said CECs have a thickness that provides an enzyme activity that is greater than the activity of the same enzyme in the CECs in a monolayer configuration on said surface of said CNT.

22. The method of claim 15, wherein said alkanol is selected from the group consisting of methanol, ethanol, 1-propanol, 2-propanol and t-butyl alcohol.

* * * * *

UNITED STATES PATENT AND TRADEMARK OFFICE
CERTIFICATE OF CORRECTION

| | | Page 1 of 1 |
|---|---|---|
| PATENT NO. | : 7,838,273 B2 | |
| APPLICATION NO. | : 12/053373 | |
| DATED | : November 23, 2010 | |
| INVENTOR(S) | : Jungbae Kim | |

It is certified that error appears in the above-identified patent and that said Letters Patent is hereby corrected as shown below:

col. 7, line 35: "6.7 mM•min1" --- should be replaced to read "6.7 mM•min-1"

col. 9, line 65: "After vigorous stirring at room temperature for 1h," --- should be replaced to read: "After vigorous stirring at room temperature for ~1h,"

col. 12, line 43: "having a platinum (Pt) loading of about 4 mg cm 2." --- should be replaced to read: "having a platinum (Pt) loading of about 4 mg·cm$^{-2}$.

col. 13, line 45: "1 claim:" --- should be replaced to read: "We claim:"

Signed and Sealed this
Eighth Day of March, 2011

David J. Kappos
*Director of the United States Patent and Trademark Office*